US010293379B2

(12) United States Patent
Justice et al.

(10) Patent No.: US 10,293,379 B2
(45) Date of Patent: May 21, 2019

(54) OBJECT DETECTION METHOD

(71) Applicants: Timothy L. Justice, Walla Walla, WA (US); Johan Calcoen, Leuven (BE); Dirk Adams, Tongeren (BE); Gerald R. Richert, Walla Walla, WA (US)

(72) Inventors: Timothy L. Justice, Walla Walla, WA (US); Johan Calcoen, Leuven (BE); Dirk Adams, Tongeren (BE); Gerald R. Richert, Walla Walla, WA (US)

(73) Assignee: Key Technology, Inc., Walla Walla, WA (US)

( * ) Notice: Subject to any disclaimer, the term of this patent is extended or adjusted under 35 U.S.C. 154(b) by 0 days.

(21) Appl. No.: 15/632,625

(22) Filed: Jun. 26, 2017

(65) Prior Publication Data
US 2018/0369870 A1    Dec. 27, 2018

(51) Int. Cl.
*B07C 5/342*    (2006.01)
*B07C 5/34*     (2006.01)
(Continued)

(52) U.S. Cl.
CPC ........... *B07C 5/3416* (2013.01); *B07C 5/10* (2013.01); *B07C 5/342* (2013.01); *B07C 5/366* (2013.01);
(Continued)

(58) Field of Classification Search
CPC ......... B07C 5/02; B07C 5/342; B07C 5/3422; B07C 5/3425; B07C 5/361;
(Continued)

(56) References Cited

U.S. PATENT DOCUMENTS 3,782,544 A * 1/1974 Perkins, III ............. A24B 1/04
                                                     209/565
3,917,070 A * 11/1975 Asfour .................... B07C 5/342
                                                     209/549
(Continued)

OTHER PUBLICATIONS

Notification of Transmittal of the International Search Report and the Written Opinion of the International Searching Authority, or the Declaration, PCT/US18/14215, dated Apr. 9, 2018.

*Primary Examiner* — Joseph C Rodriguez
(74) *Attorney, Agent, or Firm* — Randall Danskin P.S.

(57) ABSTRACT

An object detection method includes an electromagnetic radiation emitter, and an electromagnetic radiation detector on a first side of an inspection zone, a reflective background on a second side of the inspection zone and a controller operably connected to the emitter and the detector to measure/determine a first time of travel for emitted electromagnetic radiation waves/pulses to travel from the emitter, to the reflective background, and return to the detector, and to measure/determine a second time of travel for emitted electromagnetic radiation waves/pulses to travel from the emitter of electromagnetic radiation to objects of interest passing through the inspection zone along an unsupported path of travel and to be reflected to the electromagnetic radiation detector, and any determined time of travel which varies from the first time of travel is evidence there is an object within the inspection zone and between the emitter and the reflective background.

13 Claims, 6 Drawing Sheets

(51) Int. Cl.
 *G01N 21/84* (2006.01)
 *B07C 5/10* (2006.01)
 *B07C 5/36* (2006.01)

(52) U.S. Cl.
 CPC ...... *G01N 21/84* (2013.01); *B07C 2501/0018* (2013.01); *B07C 2501/0081* (2013.01)

(58) Field of Classification Search
 CPC ........ B07C 2501/0018; B07C 2501/81; G01N 2021/8455; G01N 2021/8806; G01N 2021/8848; G01N 2021/8851; G01N 2021/8901
 See application file for complete search history.

(56) References Cited

U.S. PATENT DOCUMENTS

| | | | | |
|---|---|---|---|---|
| 4,630,736 A * | 12/1986 | Maughan | ................ | B07C 5/366 209/581 |
| 5,352,888 A * | 10/1994 | Childress | .............. | B07C 5/3425 209/586 |
| 6,056,127 A * | 5/2000 | Low | .......................... | B07C 5/02 209/580 |
| 6,078,018 A * | 6/2000 | Davis | .................... | B07C 5/3416 209/580 |
| 6,497,324 B1 * | 12/2002 | Doak | ...................... | B07C 5/342 209/522 |
| 6,611,787 B2 * | 8/2003 | Stringer | ................. | G01B 11/00 702/156 |
| 8,259,298 B2 * | 9/2012 | Berghmans | ............. | B07C 5/342 356/237.1 |
| 8,283,589 B2 * | 10/2012 | Janssens | ................ | G01N 21/21 209/576 |
| 8,855,809 B2 * | 10/2014 | Spencer | ................ | B07C 5/3416 378/53 |
| 9,006,599 B2 * | 4/2015 | Adams | .................... | B07C 5/342 209/577 |
| 9,146,190 B2 * | 9/2015 | Hug | ........................ | B07C 5/342 |
| 9,676,004 B2 * | 6/2017 | Cohn | .................... | B07C 5/3425 |
| 9,795,996 B2 * | 10/2017 | Adams | ................. | B07C 5/3425 |
| 2009/0032445 A1 * | 2/2009 | Doak | ..................... | B07C 5/342 209/587 |

\* cited by examiner

OBJECT DETECTION METHOD

TECHNICAL FIELD

The present invention relates to an object detection method, and more specifically to an object detection method which includes an electromagnetic radiation emitter, a reflective background, an electromagnetic radiation detector and a controller operably connected to the emitter and the detector to measure/determine a time of travel for emitted electromagnetic radiation waves/pulses to travel from the emitter, to the reflective background, and return to the detector, which allows for detection of objects which are being sorted, and which are moving in a product stream, in a manner not heretofore possible.

BACKGROUND OF THE INVENTION

Various arrangements have been disclosed, and implemented in the last several decades, which facilitate imaging of a stream of discrete products in such a fashion that defective or unacceptable individual objects can be visually identified, and thereafter removed from the product stream so as to produce a resulting homogeneous end product stream that can then be further processed for some given end use. The various machine sorting applications that have allowed users to image, and then sort products have gained widespread usage in assorted industry segments. Further, much effort and research has been conducted in the sorting of food products in an effort to more accurately identify contamination, unripe food products, agricultural debris, foreign objects, and the like, which might have become admixed with the stream of products before final processing of the agricultural product has taken place. More accurate identification and sorting has allowed producers to engage in the sorting of bulk particulate products into differing quality categories such as when some products that may be identified as "prime" are sorted from products identified as "acceptable", which are further sorted from products identified as "unacceptable".

While great improvements have been made in various machine sorting applications through the years, shortcomings are still attendant with the use of the technology which is currently available. Chief among the shortcomings is that certain debris, foreign objects or unwanted material or unacceptable products/objects (collectively "unwanted material"), sometimes is not visually identifiable as the product stream moves through the sorting process. This may be due to any number of different conditions such as, but not limited to, for example, the unwanted material is in an improper orientation when imaged; the unwanted material has the same color as the desired product; the unwanted material has adhered to or is otherwise located in such close relationship or proximity to an acceptable product that it cannot be readily visibly discerned during the processing of the product stream; the unwanted material or debris is transparent, such as some glass and/or plastic, the unwanted material absorbs the electromagnetic radiation, the unwanted material reflects or refracts the electromagnetic radiation in a direction away from the detector, and/or the unwanted material is indistinguishable from a background such that the unwanted material is not perceptible by the sorting apparatus due to lack of contrast.

In any event, food processors, in particular, have strived to remove as much unwanted material, foreign objects, unacceptable product, and other debris from a product stream in order to ensure customer safety, and a homogenous end product for packaging and shipment. Food processors, for example, further want to ensure that the processing equipment does not produce excessive "false rejects." These "false rejects" are acceptable product that has been mistakenly identified as unacceptable by the sorting system. This, of course, reduces the waste from the product stream, and also ensures that the food processor can receive the maximum available profit from the product stream being processed.

An object detection method and apparatus which avoids the detriments associated with the prior art apparatus and methods, which have been utilized heretofore, is the subject matter of the present patent application.

SUMMARY OF THE INVENTION

A first aspect of the present invention relates to a method for detecting objects of interest that includes the steps of releasing a stream of individual objects of interest from a conveying device into an unsupported gravity influenced path of travel; providing an inspection zone having opposite first and second sides and opposing first and second edges and locating the inspection zone downstream of a position where the stream of individual objects of interest are released for movement along the unsupported path of travel, and orienting the path of travel so that the path of travel passes through the inspection zone and between the opposite first and second sides and between the opposite first and second edges thereof; positioning an emitter of electromagnetic radiation on the first side of the inspection zone, and further periodically energizing the emitter of electromagnetic radiation to generate a pulsed emission of electromagnetic radiation which traverses the inspection zone, and directing the pulsed emitted electromagnetic radiation towards the second side of the inspection zone, and wherein at least a portion of the pulsed emitted electromagnetic radiation strikes at least one of the individual objects of interest traveling along the unsupported path of travel, and through the inspection zone; positioning a reflective background adjacent to the second side of the inspection zone and at a known distance from the emitter of electromagnetic radiation, and wherein the reflective background reflects at least a portion of the pulsed emitted electromagnetic radiation back in the direction of the first side of the inspection zone; providing a detector of electromagnetic radiation, and positioning the detector of electromagnetic radiation on the first side of the inspection zone, and at a known distance from the reflective background, and wherein the detector of electromagnetic radiation receives, and detects, at least a portion of the pulsed electromagnetic radiation which is emitted by the periodically energized emitter of electromagnetic radiation, and which has further been reflected, at least in part, back in the direction of the first side of the inspection zone by either the reflective background, or by at least one of the individual objects of interest, as the respective objects of interest pass through the inspection zone and along the unsupported path of travel; providing a controller and operatively coupling the controller with both the emitter of electromagnetic radiation and the detector of electromagnetic radiation; determining by use of the controller, a first time of travel for each pulse of the emitted electromagnetic radiation to travel from the periodically energized emitter of electromagnetic radiation the known distance to the reflective background and to travel the known distance from the reflective background to the detector of electromagnetic radiation after being at least partially reflected by the reflective background; determining by use of the controller, a second time of travel for each pulse of the emitted electromagnetic radiation which is directed towards, and strikes at least one of the respective objects of interest moving through the inspection zone along the unsupported path of travel, to travel from the emitter of electromagnetic radiation to the at least one object of interest, and to travel from at least one object of interest back to the detector of electromagnetic radiation, and which second time of travel varies from the first time of travel; and determining, by use of the controller, the presence of an object of interest within the inspection zone when the determined second time of travel varies from the determined first time of travel.

A second aspect of the present invention relates to a method for detecting objects of interest passing through an inspection zone having the steps of; providing a stream of individual objects of interest, and wherein each of the individual objects of interest have a multitude of characteristics, and wherein the multitude of characteristics of the individual objects of interest in the stream are selected from the group comprising color, length, width, thickness, shape, light polarization, florescence, surface texture, reflectivity, light absorbance, light translucence, and wherein the characteristics can be formed from electromagnetic radiation which is spectrally reflected, refracted, absorbed or transmitted; moving the stream of individual objects of interest along a first supported path of travel from a first position to a second position, and wherein the step of moving the stream of individual objects of interest to the inspection zone further comprises releasing the stream of individual objects of interest from the second position into an unsupported path of travel through the inspection zone that has spaced apart and opposing first and second sides and spaced apart and opposing first and second edges; providing an emitter of electromagnetic radiation adjacent the first side of the inspection zone that, when actuated, generates pulses of electromagnetic radiation which are directed toward the opposing second side of the inspection zone and toward the unsupported moving stream of individual objects of interest so that the electromagnetic radiation pulses impact one or more of the individual objects of interest passing through the inspection zone, or the electromagnetic radiation pulses pass completely through the unsupported stream and strike a reflective background which is positioned adjacent the second side of the inspection zone and at a known distance from the emitter of electromagnetic radiation, and the electromagnetic radiation pulses striking the reflective background are at least partially reflected back toward the first side of the inspection zone; providing a detector of electromagnetic radiation positioned adjacent the first side of the inspection zone and oriented to receive electromagnetic radiation pulses reflected by the reflective background and/or reflected by striking at least one of the individual objects of interest within the inspection zone, and the detector of electromagnetic radiation is positioned a known distance from the reflective background; providing a controller operative communicating with the emitter of electromagnetic radiation and operatively communicating with the detector of electromagnetic radiation to provide signals to the emitter of electromagnetic radiation and to receive signals from the detector of electromagnetic radiation so as to determine a time duration between emission of electromagnetic radiation pulses from the emitter, and receipt of reflected electromagnetic radiation pulses by the detector, and wherein any determined time duration that varies from a known time duration for the emitted electromagnetic radiation pulses to travel both from the emitter to the reflective background and from the reflective background back to the detector indicates an object of interest is present within the inspection zone; forming in real time, a multiple aspect representation of the individual objects of interest moving in the unsupported product stream within the inspection zone with the controller by using signals generated by the electromagnetic radiation detector and wherein the multiple aspect representation has a plurality of features formed from a multitude of electromagnetic wave lengths detected by the detector; comparing, with the controller, identified characteristics of each of the individual objects of interest in the unsupported stream of objects of interest within the inspection zone to a predetermined list of acceptable and unacceptable characteristics in order to make a sorting decision for sorting the objects of interest within the unsupported product stream; and providing an ejector having a plurality of high pressure air nozzles coupled with a source of high pressure air and which further is positioned downstream of the inspection zone and wherein the ejector is operatively coupled with the controller which individually activates and deactivates the high pressure air nozzles of the ejector and wherein the high pressure air nozzles, upon receiving the signal release a stream of high pressure air which strikes and removes identified individual objects of interest from the unsupported stream of objects of interest that have been identified by the controller as having predetermined unacceptable characteristics during the unsupported path of travel based, at least in part upon, the multiple aspect representation formed by the controller, in real time, as the individual objects of interest pass through the inspection zone.

A third aspect of the present invention relates to a method of detecting objects passing through an inspection zone wherein the controller learns that repetitive infinite measures occurring at an identified location on the reflective background represent a defect in the reflective background, and therefore that repeated infinite measures at that identified location should be disregarded by the controller when a sorting decision is made.

A fourth aspect of the present invention relates to an apparatus for detecting objects of interest passing through an inspection zone comprising a device for conveying a stream of individual objects of interest and for releasing the stream of individual objects of interest into a gravity influenced unsupported path of travel; an inspection zone having opposite first and second sides and spaced apart opposing first and second edges, and which is located downstream of the device for conveying the stream of individual objects of interest, and wherein the path of travel passes through the inspection zone between the opposite first and second sides and between the first and second edges thereof; an emitter of pulsed electromagnetic radiation positioned on the first side of the inspection zone, and which further, when periodically energized, emits a pulse of electromagnetic radiation which traverses the inspection zone, and is further directed towards the opposite, second side of the inspection zone, and wherein at least a portion of the emitted electromagnetic radiation pulse strikes at least one of the individual objects of interest traveling along the unsupported path of travel through the inspection zone; a reflective background positioned adjacent to the second side of the inspection zone, and wherein the reflective background is located at a known distance from the emitter of electromagnetic radiation, and further the reflective background reflects at least a portion of the emitted electromagnetic radiation pulse back in the direction of the first side of the inspection zone; a detector of electromagnetic radiation positioned on the first side of the inspection zone which receives, and detects, at least a portion of the electromagnetic radiation pulse which is emitted by the periodically energized emitter of electromagnetic radiation, and which has further been reflected, at least in part, back in the direction of the first side of the inspection zone by either the reflective background, or by at least one of the individual objects of interest, as the individual objects of interest pass through the inspection zone, and along the unsupported path of travel, and wherein a first time of travel is determined for each pulse of emitted electromagnetic radiation to travel from the periodically energized emitter of electromagnetic radiation the known distance to the reflective background and to travel the known distance from the reflective background to the detector of electromagnetic radiation after being, at least partially, reflected by the reflective background, and wherein a second time of travel is determined for each pulse of emitted electromagnetic radiation to travel from the periodically energized emitter of electromagnetic radiation to an object of interest moving along the unsupported path of travel and to be reflected therefrom, and to travel back to the detector of electromagnetic radiation and wherein the second time of travel varies from the first time of travel; a controller operatively coupled with both the emitter of electromagnetic radiation and the detector of electromagnetic radiation, and wherein any time of travel which varies from the first time of travel is evidence to the controller that an object of interest is within the inspection zone; and an ejector having a plurality of high pressure air nozzles, coupled with a source of high pressure air and which further is positioned downstream of the inspection zone, and wherein the ejector is operatively coupled with the controller which individually activates and deactivates the high pressure air nozzles of the ejector, and wherein the high pressure air nozzles release a stream of high pressure air which removes identified individual objects of interest from the stream of objects of interest that have been identified by the controller as having predetermined unacceptable characteristics during the unsupported path of travel.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
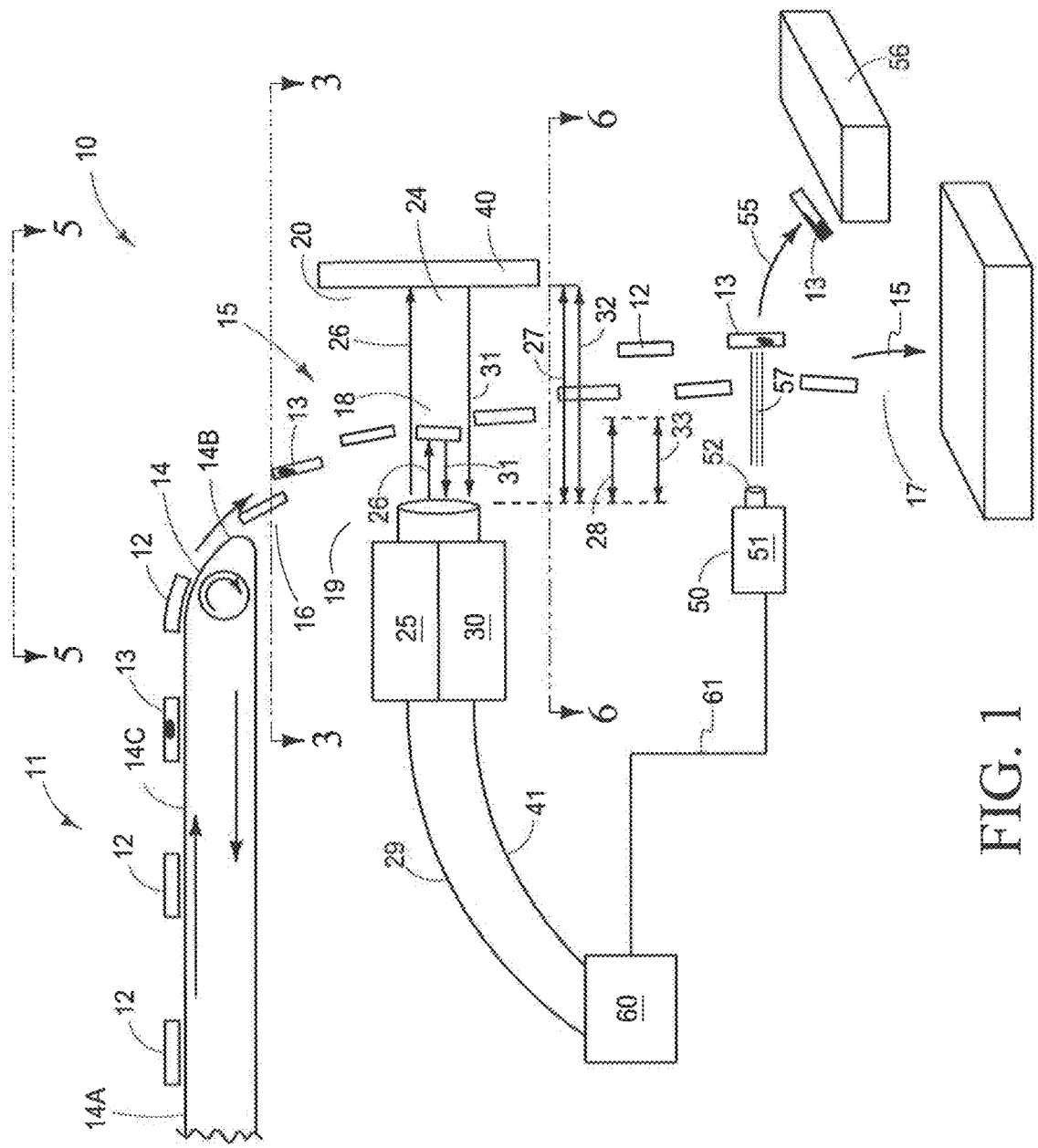
FIG. 1 is a greatly simplified orthographic side view exploded block diagram of the object detection method and apparatus of the present invention showing objects of interest being released into an unsupported path of travel, an emitter of electromagnetic radiation, a detector of electromagnetic radiation, a reflective background and an ejector removing identified objects of interest from the product stream.

Referring now to FIG. 1, a greatly simplified view of the object detection method and apparatus of the present invention is seen. In this regard the object detection apparatus is generally indicated by the numeral 10, and is used to determine the presence, and position of discrete individual objects of interest 11 and then to sort the discrete individual objects of interest 11 based upon predetermined parameters. The discrete individual objects of interest 11 can include any number of different items, such as discreet food products, or other manufactured objects. It should be understood that the source of objects 11 includes both acceptable objects/products 12, and some number of unacceptable objects/products 13. The unacceptable objects/products 13 may include products that do not meet the specified need or requirements or characteristics of a processor, or on the other hand could constitute some type of contamination or other unwanted material. More specifically, the unacceptable objects or products 13 may include individual objects of interest 11 that are not perceptible by the imaging means ("invisible" to the imaging means) due to characteristics such as having the same color as a background, because of being transparent, because of being completely opaque and thus absorbing electromagnetic radiation, or for spectrally reflecting/refracting electromagnetic radiation in directions other than toward a detector. In the case of natural food products, such contamination could include agricultural debris, natural or synthetic materials which are associated with harvesting activities, broken glass, plastic, rocks, animal debris, and any number of other unacceptable materials that may have become admixed with the steam of objects of interest 11. Further, such contamination need not be an entire object of interest 11, but may be only a portion of an object of interest 11, such as, but not limited to, an area of "rot" (not shown) on an otherwise acceptable object of interest 11.

As best seen from a study of FIG. 1, a source of objects 11 to be sorted are supplied or provided to the object detection apparatus 10 by means of a delivery device 14, which is here depicted as a continuous conveyor which has a first product receiving end 14A, a second spaced apart product discharge end 14B and further has a top flight 14C that moveably supports the objects 11 to be sorted. The delivery device 14 may also include other structures such as slides, shoots, and other conventional means for placing the source of objects 11 to be sorted into a continuous stream so that the objects 11 to be sorted can be moved along in a given direction, and then released into an unsupported, gravity influenced, path of travel 15. The unsupported path of travel 15 (or trajectory) has a first end 16 which is located adjacent to the second discharge end 14B of the delivery device 14, and a remote, second end 17, which is located elevationally below, the discharge end 14B of the delivery device 14.

An inspection zone 18 having a first side 19, a spaced apart second side 20, a first edge 20A and a spaced apart second edge 20B (FIG. 3) is located spacedly adjacent and vertically below the product discharge end 14B of the delivery device 14, and is substantially vertically oriented so that the unsupported path of travel 15 passes through the inspection zone 18 and between the first side 19 and the second side 20 and between the first and second edges 20A, 20B respectively. The inspection zone 18 provides a field of view 24 for an electromagnetic radiation emitter 25 and for an electromagnetic radiation detector 30 which will be discussed in more detail below.

The electromagnetic radiation emitter 25 is positioned adjacent the first side 19 of the inspection zone 18 and is oriented so that emitted electromagnetic waves/pulses 26 are transmitted toward the second side 20 of the inspection zone 18 and transversely across the inspection zone 18 and field of view 24. It is to be understood that in a preferred embodiment, the emitted electromagnetic radiation waves/pulses 26 are emitted as a line scan (a "flying spot") from the electromagnetic radiation emitter 25 and the emitted electromagnetic waves/pulses 26 sweep across the inspection zone 18 from one edge 20A to the spaced apart opposing edge 20B. It should further be understood that the emitted electromagnetic waves/pulses 26 may be of various wavelengths and may be visible, invisible, or both, and may be in various and specific predetermined wavelength "ranges" or "bands" and further the waves/pulses 26 may be sequential or temporally spaced by time in order to react in specific predictable ways with various of the multitude of characteristics of the individual objects of interest 11, for example in order to maximize discernment and machine/imaging visualization of characteristics such as, but not limited to, color, length, width, depth, thickness, shape, light polarization, fluorescence, surface texture, reflectivity, light absorbance, light translucence, and the like. The emitted waves/pulses 26 may further be temporally spaced in time in order to avoid destructive interference that may occur when emitted electromagnetic waves/pulses 26 have wavelength ranges/bands that "overlap" or are too broad to allow precise distinguishment and/or discernment and/or perceptibility of various characteristics that are to be inspected. Further still, it is to be understood that the emitted electromagnetic waves/pulses 26 are emitted in a direction so as to traverse and sweep repeatedly from edge 20A to edge 20B across the unsupported path of travel 15, as the objects of interest 11 pass between the first side and second side 19, 20 respectively of the inspection zone 18. The electromagnetic radiation emitter 25 is operatively coupled to, and controlled by a controller 60 in a manner which will be discussed in detail below.

The invention further includes a reflective background 40 which is located a known distance 27 from the electromagnetic radiation emitter 25, and on the second side 20 of the inspection zone 18 so as to receive emitted electromagnetic waves/pulses 26 emitted from the electromagnetic radiation emitter 25. The reflective background 40 is formed of a known reflective material such as, but not limited to, plastic, PTFE (also known as Teflon®), polyester, or acetyl (also known as Delrin®) that reflects electromagnetic waves/pulses 26, is durable, and is not subject to damage by cleaning and is resistant to the adherence of debris, such as food product splatter and the like. In this spatial arrangement, the objects of interest 11 which are passing through the inspection zone 18 move along the unsupported path of travel 15 between the electromagnetic radiation emitter 25 and the reflective background 40. The reflective background 40 receives the emitted electromagnetic waves/pulses 26 which have passed through the inspection zone 18 and which further have not been reflected by/from any objects of interest 11. When the emitted electromagnetic waves/pulses 26 strike the reflective background 40, the reflective background 40 reflects and redirects at least a portion of the striking emitted electromagnetic waves/pulses 26 (reflected electromagnetic waves 31) along a return path of travel back toward the first side 19 of the inspection zone 18 and toward an electromagnetic radiation detector 30 which is positioned on the first side 19 of the inspection zone 18.

As can be seen from a review of FIG. 1, some portion of the emitted electromagnetic waves/pulses 26 emitted by the electromagnetic radiation emitter 25 and directed across the inspection zone 18 and the unsupported path of travel 15 strike, or otherwise impact at least one of the plurality of objects of interest 11 passing along the unsupported path of travel 15 within the inspection zone 18. Distance 28 is defined between the electromagnetic radiation emitter 25 and the objects of interest 11 within the inspection zone 18 and passing along the unsupported path of travel 15 that are struck, or otherwise impacted by the emitted electromagnetic waves/pulses 26.

Reflected electromagnetic waves 31 that have struck/impacted the reflective background 40 and have been reflected, and redirected at least partially back toward the first side 19 of the inspection zone 18, and toward the electromagnetic radiation detector 30 are shown in FIG. 1. Further, reflected electromagnetic waves 31 that have struck objects of interest 11 passing along the unsupported path of travel 15, and within the inspection zone 18 are similarly shown in FIG. 1.

The electromagnetic radiation emitter 25 is operatively coupled with the controller 60, so that the electromagnetic radiation emitter 25 emits an emitted electromagnetic wave/pulse 26, each time an emission signal 29 (also known as a "sync signal") is communicated to the electromagnetic radiation emitter 25 by the controller 60. By this means, the controller 60 "drives" the emission of the electromagnetic waves/pulses 26.

Figure 2:
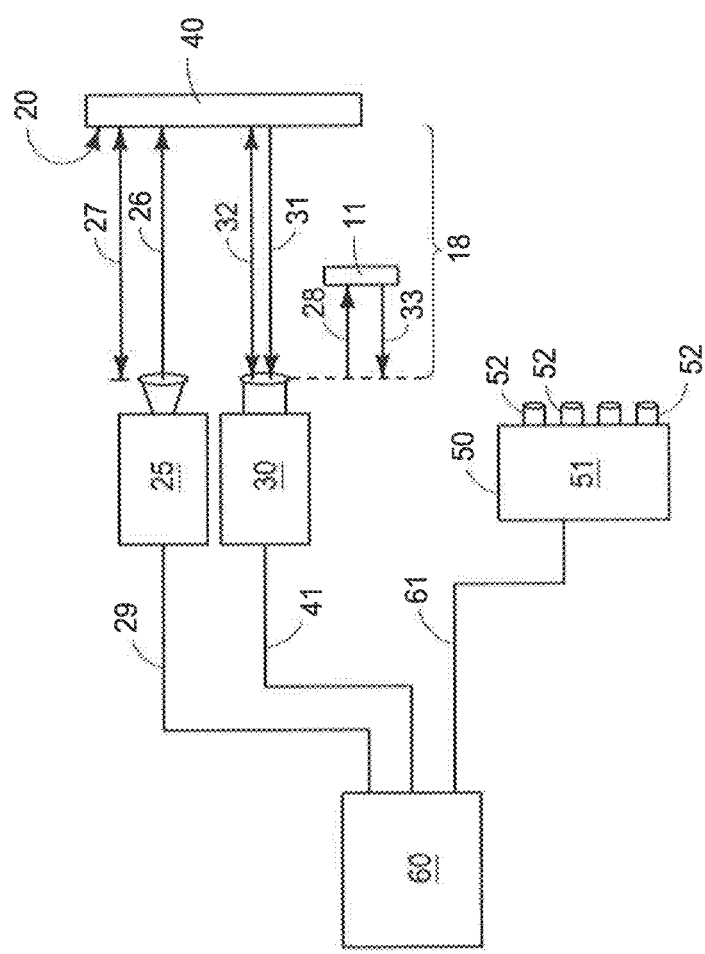
FIG. 2 is a simplified block diagram of the components of the instant invention showing the emitter of electromagnetic radiation and the detector of electromagnetic radiation as physically separate devices.

The present invention further includes an electromagnetic radiation detector 30 which may be, but is not limited to, a Photo Multiplier Tube (PMT); an Avalanche Photo Diode (APD); a Silicone Photo Multiplier (SiPM); an InGaAs detector; a camera, or other type of device capable of detecting and receiving reflected electromagnetic radiation waves/pulses 31. The electromagnetic radiation detector 30, as shown in FIGS. 1 and 2, is positioned adjacent the electromagnetic radiation emitter 25, and is positioned on the first side 19 of the inspection zone 18 although it is contemplated the electromagnetic radiation detector 30 may be located/positioned in a different location, and it is further contemplated the emitter 25 and the detector 30 may be combined into a single scanning device (FIG. 3) so that the emitted electromagnetic waves/pulses 26 and the reflected electromagnetic waves/pulses 31 are coincident.

The electromagnetic radiation detector 30 is oriented to receive reflected electromagnetic waves/pulses 31 that have been reflected by both the reflective background 40 and also reflected by striking/impacting objects of interest 11 passing along the unsupported path of travel 15 through the inspection zone 18. Distance 32 between the electromagnetic radiation detector 30 and the reflective background 40 is known. Distance 33 between the electromagnetic radiation detector 30 and the objects of interest 11 within the inspection zone 18 is variable and is unknown, however distance 33 will always be less than distance 32.

Because the speed of electromagnetic radiation in air is constant, and because distance 27 between the electromagnetic radiation emitter 25 and the reflective background 40 is known, and because the distance 32 between the electromagnetic radiation detector 30 and the reflective background 40 is known, a first time of travel $t_1$ (FIG. 4) may be calculated for each emitted electromagnetic wave/pulse 26 to travel from the electromagnetic radiation emitter 25 across the inspection zone 18 to the reflective background 40, and thereafter to be reflected from the reflective background 40 back to the electromagnetic radiation detector 30.

Similarly, a second time of travel $t_2$ (FIG. 4) may be calculated because emitted electromagnetic radiation waves/pulses 26 emitted by the emitter 25 may strike objects of interest 11 passing along the path of travel 15 through the inspection zone 18 and be at least partially reflected therefrom back to the electromagnetic radiation detector 30 where the reflected electromagnetic waves 31 are detected. Therefore the second time of travel $t_2$ may be calculated and the second time of travel $t_2$ is less than the first time of travel $t_1$.

A reflection receipt signal 41 is generated by the electromagnetic radiation detector 30 each time a reflected electromagnetic radiation wave/pulse 31 is received by the electromagnetic radiation detector 30. The reflection receipt signal 41 is communicated to the controller 60.

Figure 4:
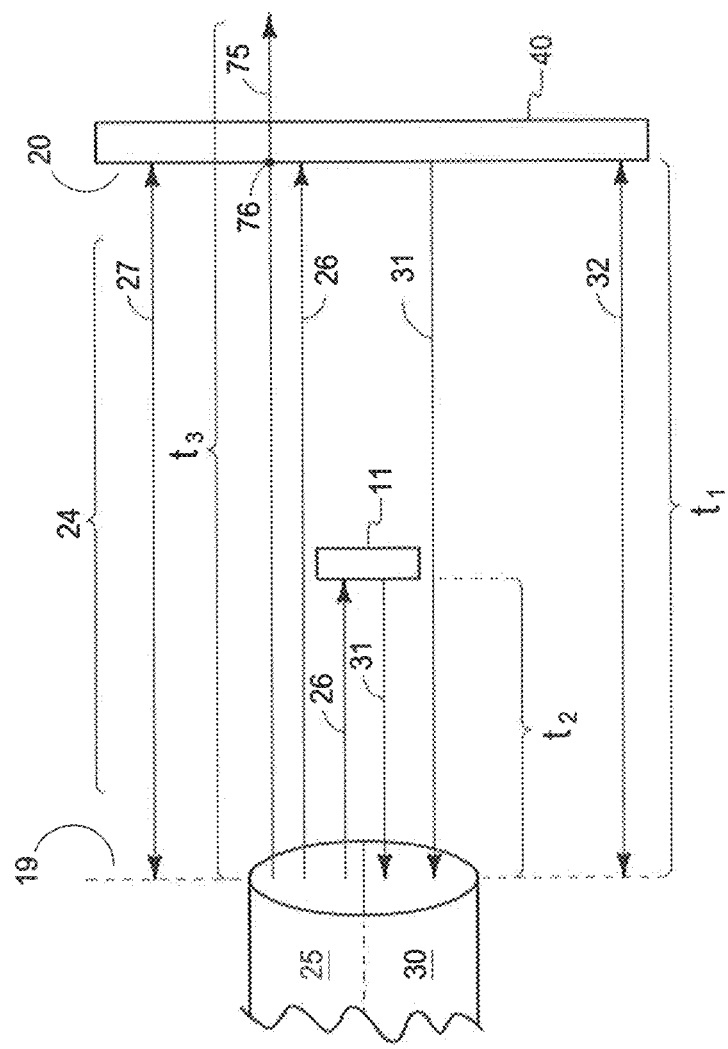
FIG. 4 is an enlarged view of a portion of FIG. 1 showing distances representing the first time of travel $t_1$ and the second time of travel $t_2$.
Figure 5:
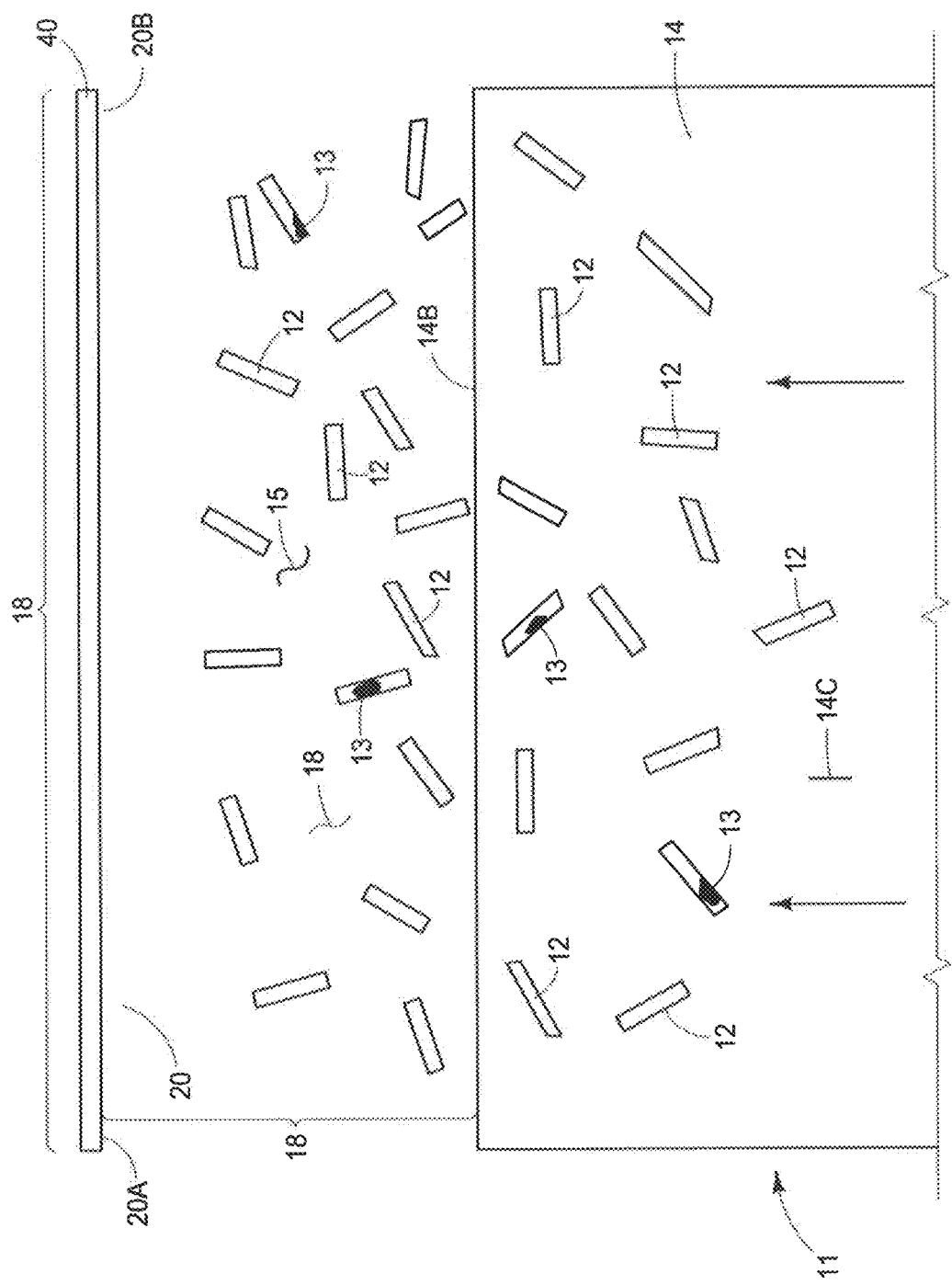
FIG. 5 is a downwardly looking plan view, taken on line 5-5 of FIG. 1, and rotated 90 degrees counter-clockwise, showing a plurality of individual objects of interest being released from the conveyor means and into the unsupported path of travel for simultaneous passage through the inspection zone.

The controller 60, is operatively connected to the electromagnetic radiation emitter 25 to provide an emission signal 29 (a sync signal) to the electromagnetic radiation emitter 25, and also operatively connected to the electromagnetic radiation detector 30, so as to receive reflection receipt signals 41 therefrom. The controller 60 uses the emission signals 29 and reflection receipt signals 41 to calculate the first time of travel $t_1$ and also to calculate the second time of travel $t_2$ (FIG. 4). Calculation of the first time of travel $t_1$ by the controller 60 is evidence that there is no object of interest 11 within the inspection zone 18 between the electromagnetic radiation emitter 25 and the reflective background 40. The calculation of a second time of travel $t_2$ by the controller 60, on the other hand, supports a decision by the controller 60 that there is an object of interest 11 within the inspection zone 18 between the electromagnetic radiation emitter 25 and the reflective background 40. The calculation of the first time of travel $t_1$, and the calculation of the second time of travel $t_2$, or the absence of any reflected electromagnetic radiation wave/pulse 31 allows the controller 60 to confirm the presence of, or absence of, an object of interest 11 within the inspection zone 18 in support of making a sorting decision and whether to generate an ejection signal 61 if so required.

Figure 6:
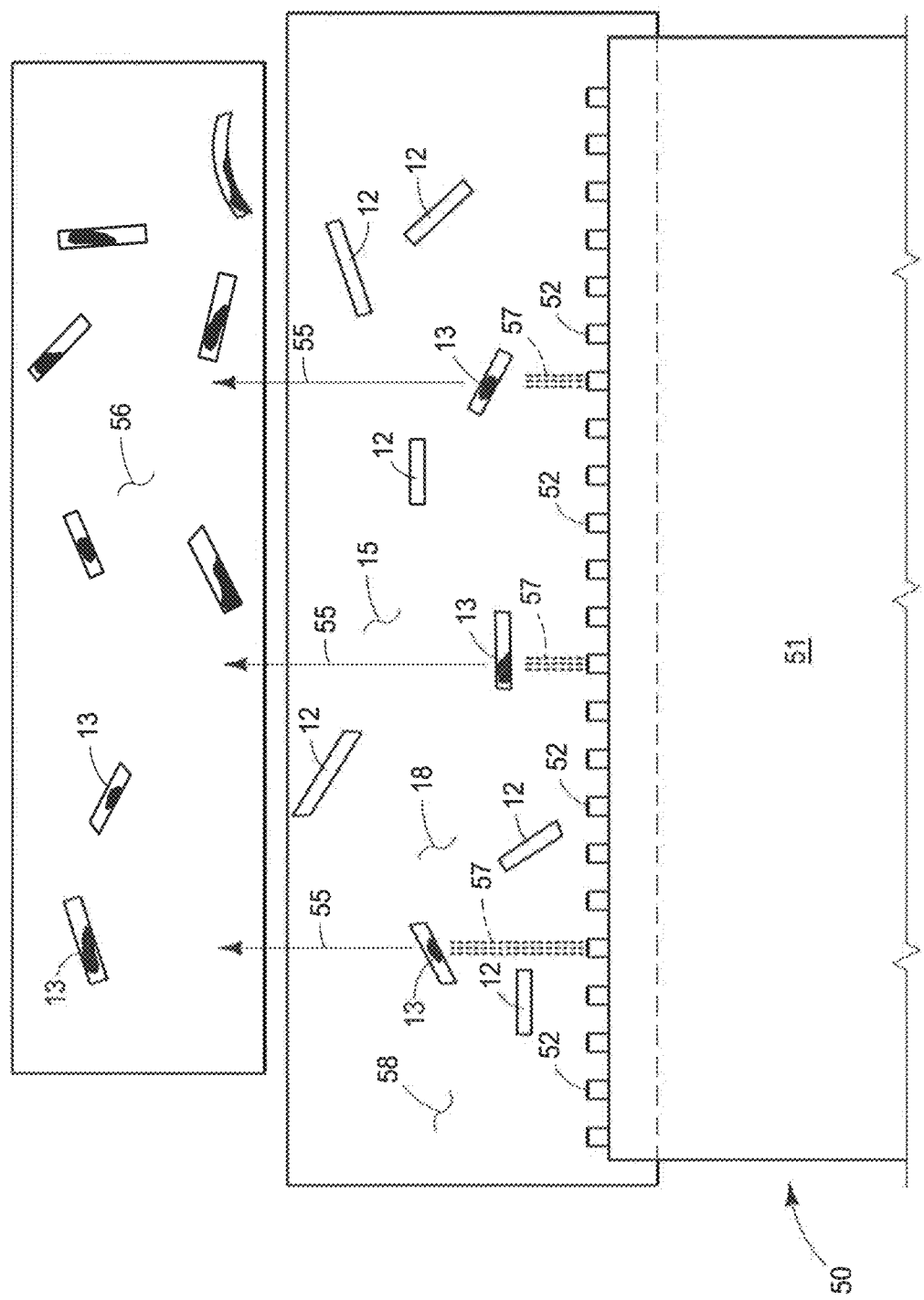
FIG. 6 is a downwardly looking, plan view, taken on line 6-6 of FIG. 1 and rotated 90 degrees counter-clockwise, showing the ejector sorting identified objects of interest from the product stream during the unsupported path of travel.

As shown in FIGS. 1 and 2, the present invention further includes an ejector 50 which is positioned downstream relative to the inspection zone 18 and at a location which is near the second end 17 of the unsupported path of travel 15. The ejector 50 is of traditional design, and is further operatively coupled in signal receiving relation relative to the controller 60. The ejector 50 includes an ejector manifold 51 that defines a multiplicity of individual air discharge nozzles 52. The ejector 50 is further supplied with a source of pressurized air (not shown) and which is then selectively discharged as indicated by the number 57, in order to exert force on an identified unacceptable product 13 which is moving along the unsupported path of travel 15. The release of pressurized air 57 from one or more individual air discharge nozzles 52 "knocks" or otherwise exerts a force on, the unacceptable product 13 to move the object 13 out of the unsupported path of travel 15 and into a second path of travel 55. (FIG. 6). The ejector 50 may be selectively actuated by means of the controller 60, after the controller 60 has detected the presence of an object of interest 11 and characterizes the object of interest 11 as acceptable 12 or unacceptable 13.

As noted previously, the present invention is contemplated to be employed in conjunction with a machine imaging and sorting apparatus (not shown) that employs photo optic sensors to rapidly image and scan a plurality of individual objects of interest 11 simultaneously passing along the unsupported path of travel 15 through the inspection zone 18 preferably prior to, or coincident with the instant electromagnetic radiation emitter 25. As noted previously, one of the known difficulties with known photo optic imaging and sorting systems of bulk particulate such as, but not limited to, peas, grapes, potato strips, potato slices, beans, and the like, occurs when unacceptable material (generally an unacceptable object 13) passes through the inspection zone 18 along with acceptable objects 12, and the unacceptable object 13 has the same color as the reflective background 40; the unacceptable object 13 completely absorbs the electromagnetic radiation; the unacceptable object 13 reflects/refracts the electromagnetic radiation 26 in a direction other than toward the detector 30; or the unacceptable object 13 is otherwise "invisible" to the scanning and imaging systems employed, in the sense that the object of interest 11 is indistinguishable from the reflective background 40, or stated another way, the sorting apparatus (not shown) is unable to discern the unacceptable object of interest 13 from the reflective background 40 because there is no contrast between the unacceptable object 13 and the reflective background 40. When such an "invisible" unacceptable object 13 passes through the inspection zone 18, known imaging and sorting systems are unable to distinguish or discern the unacceptable object 13 from the reflective background 40, and therefore the unacceptable objects 13 pass through the inspection zone 18 along with the acceptable objects 12, thus contaminating the end product stream of acceptable products 12.

The present invention provides a redundant sorting methodology which employs the first time of travel $t_1$ and the second time of travel $t_2$ of emitted and reflected electromagnetic waves/pulses 26, 31 respectively, or a moving location that generates an absence of a reflected electromagnetic wave/pulse 31. Information regarding the first time of travel $t_1$, and the second time of travel $t_2$, or absence of a reflected wave/pulse 31 is utilized in conjunction with the controller's 60 sorting decisions based upon predetermined sorting criteria stored in the controller 60 and the multitude of characteristics of the individual objects of interest 11 within the product stream so that when the optical imaging and sorting system (not shown) is unable to distinguish an object of interest 11 passing through the inspection zone 18 from the reflective background 40, and therefore cannot make a sorting decision thereon, the present invention's determination of a second time of travel $t_2$, or a moving location that generates an absence of reflected electromagnetic radiation 31 indicates that "something" is present in the inspection zone 18 despite the fact the optical imaging system (not shown) is unable to distinguish or identify the object 11. Because the controller 60, based upon the second time of travel $t_2$, or identified moving location that generates an absence of reflected electromagnetic radiation wave/pulse 31, is able to determine a non-identified "something" is present in the inspection zone 18, the controller 60 can generate an ejection signal 61 that is communicated to the ejector 50 to remove the non-identified "invisible" object passing through the inspection zone 18. As such, the present invention 10 provides safety and redundancy for optical sorting systems to allow such systems to identify the presence of otherwise "invisible" objects within the stream of products that would otherwise pass through the inspection zone 18.

Figure 3:
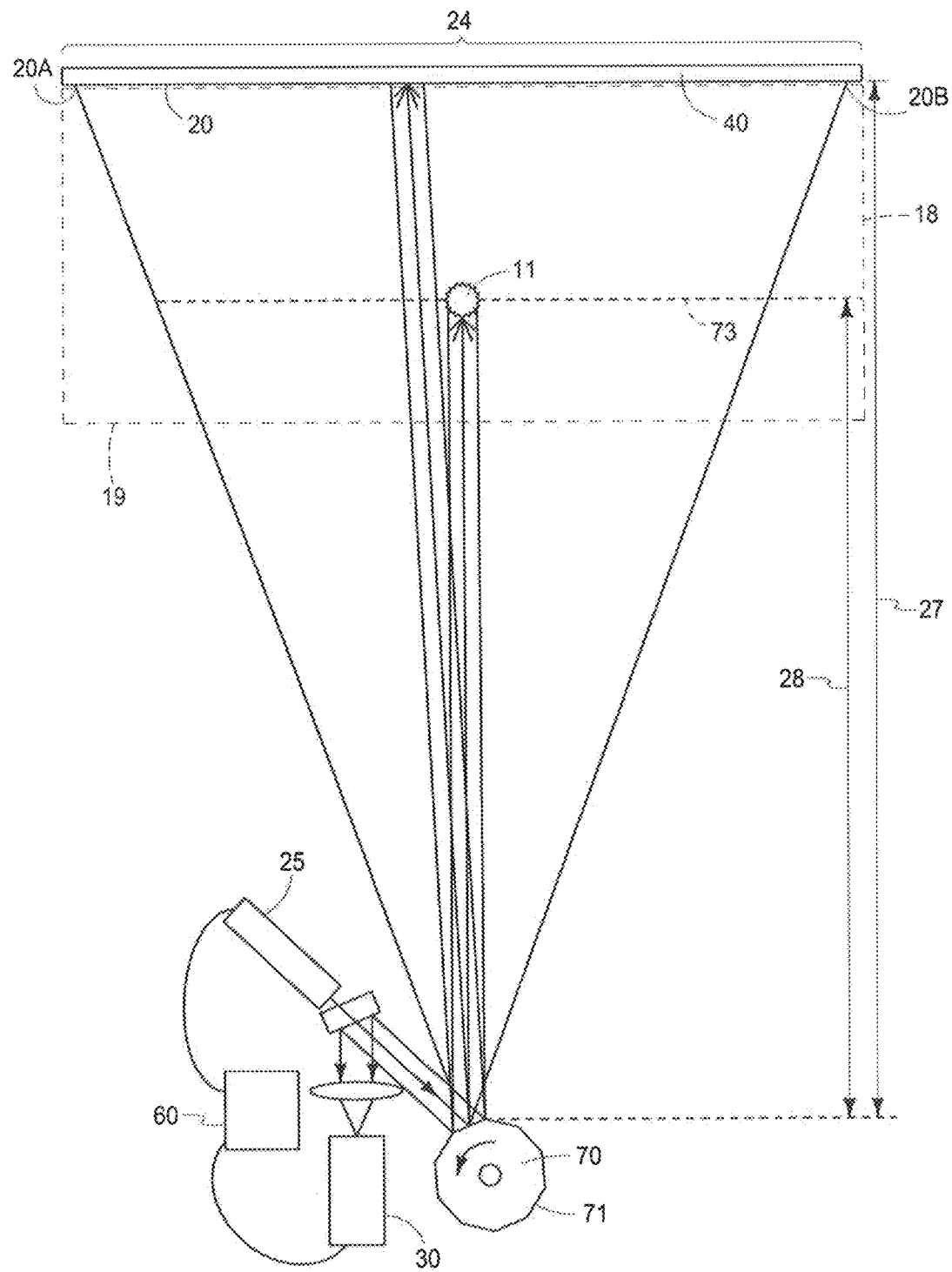
FIG. 3 is a detailed drawing of the internal components of a scanning device, taken on line 3-3 of FIG. 1, showing a polygon mirror, an emitter of electromagnetic radiation and a detector of electromagnetic radiation showing pulses of electromagnetic radiation traveling to and from the reflective background and through the inspection zone.

Referring now to FIG. 3, and in one possible form of the invention, the electromagnetic radiation emitter 25 generates the electromagnetic radiation waves/pulses 26 as a line scan across the field of view 24 by means of a rotating polygon 70 of conventional design. Rotating polygons 70 which produce a scanning or "flying spot" have been widely used for many years. The rotating polygon 70 has an exterior facing surface 71, which defines a multiplicity of reflective facets. The rotation of the polygon 70 produces an illuminated scanning line 73 which moves across the reflective background 40 in a manner which is well known in the art. As seen in FIG. 3, the electromagnetic radiation detector 30 may be positioned spacedly adjacent the rotating polygon 70 and is operable to collect or receive the reflected electromagnetic radiation waves/pulses 31 which are reflected from the objects of interest 11, or are reflected by the reflective background 40 on the second side 20 of the inspection zone 18. It should also be noted that although the Figures, for ease of understanding, show the emitter 25 and the detector 30 as spatially separated from one another, the emitter 25 and the detector 30 may preferably be coincident and collinear.

Operation

The operation of the described embodiment of the present invention is believed to be readily apparent, and is briefly summarized at this point. In its broadest aspect the present invention relates to a method and apparatus for detecting objects of interest 11 which includes an electromagnetic radiation emitter 25 for generating emitted electromagnetic waves/pulses 26 which are transmitted generally transversely across the inspection zone 18 from the first side 19 of the inspection zone 18 to the second side 20 of the inspection zone 18 and sweeping from a first edge 20A to the spaced apart opposing second edge 20B. A plurality of individual objects of interest 11 move, under the influence of gravity, along an unsupported path of travel 15 that passes through the inspection zone 18 between the first side 19 and the second side 20 and between the first edge 20A and the second edge 20B thereof. The emitted electromagnetic wave/pulses 26 strike, or otherwise impact at least some of the individual objects of interest 11 passing along the path of travel 15 through the inspection zone 18. Further, at least some of the emitted electromagnetic waves/pulses 26 pass completely through the inspection zone 18 to the second side 20 of the inspection zone 18 whereupon the emitted electromagnetic waves/pulses 26 strike and are reflected by the reflective background 40 that is positioned at the second side 20 of the inspection zone 18. The reflective background 40 is positioned a known distance 27 from the electromagnetic radiation emitter 25. The emitted electromagnetic waves/pulses 26 that strike the reflective background 40, are reflected therefrom, at least partially back toward the first side 19 of the inspection zone 18 and generally transversely across the inspection zone 18. The reflected electromagnetic waves 31 are at least partially received by the electromagnetic radiation detector 30 that is positioned on the first side 19 of the inspection zone 18.

The electromagnetic radiation emitter 25 and the electromagnetic radiation detector 30 are both operatively coupled to the controller 60. Further, the controller 60 periodically emits an emission signal 29 (a sync signal) that is communicated to the electromagnetic radiation emitter 25 which causes the electromagnetic radiation emitter 25 to responsively emit an electromagnetic radiation wave/pulse 26. Similarly, the electromagnetic radiation detector 30 generates a reflection receipt signal 41 each time the electromagnetic radiation detector 30 receives a reflected electromagnetic wave/pulse 31 and the reflection receipt signal 41 is communicated to the controller 60.

As shown in the drawings, the electromagnetic radiation detector 30 receives reflected electromagnetic waves/pulses 31 that are reflected from both the reflective background 40 and also reflected from individual objects of interest 11 passing through the inspection zone 18 which are impacted by the emitted electromagnetic wave/pulses 26. Because both the electromagnetic radiation emitter 25 and the electromagnetic radiation detector 30 are positioned a known distance 27, 32 from the reflective background 40, and because electromagnetic radiation pulses 26 travel at a constant speed in air, the controller 60 is able to determine a first time of travel $t_1$ for emitted electromagnetic waves/pulses 26 to travel from the electromagnetic radiation emitter 25, to the reflective background 40 and then back to the electromagnetic radiation receiver 30. Determination of the first time of travel $t_1$ is evidence that there is no object of interest 11 within the inspection zone 18 between the electromagnetic radiation emitter 25 and the reflective background 40. Similarly, the controller 60 is able to determine a second time of travel $t_2$, which is shorter in duration than the first time of travel $t_1$, when the electromagnetic radiation detector 30 receives a reflected electromagnetic wave/pulse 31 that has been reflected, at least in part, by an object of interest 11 within the inspection zone 18. The shorter (less duration) second time of travel $t_2$ is evidence that there is an object of interest 11 within the inspection zone 18 between the electromagnetic radiation emitter 25 and the reflective background 40.

Further still, there may be circumstances where the emitter of electromagnetic radiation 25 emits an electromagnetic pulse 26 responsive to a sync signal 29 but no reflected electromagnetic wave/pulse 31 is received or detected by the detector of electromagnetic radiation 30. (Stated another way, there is an absence of any reflected wave/pulse 31.) As noted herein, such a circumstance may occur if there is a defect 76 in the reflective background 40, such as but not limited to a hole therein or a scratch or debris. Such a circumstance may also occur if an unacceptable object of interest 13 moving through the inspection zone 18 absorbs or reflects/refracts the emitted electromagnetic radiation wave/pulse 26 in a direction other than toward the electromagnetic radiation detector 30. In this possible circumstance the location of the absence of reflected electromagnetic radiation wave/pulse 31 will move with the unacceptable object 13 as the unacceptable object 13 moves through the inspection zone 18 and the controller 60 will detect that movement through the inspection zone 18 to generate an appropriate ejection signal 61.

The signals communicated by the controller 60 to the emitter 25 and from the detector 30 to the controller 60 are evaluated by the controller 60 examining an initial leading edge of each signal 29, 41. Each signal is characterized as a "square wave" that shows a distinct vertical change at the leading edge of the signal.

The controller 60, which works in cooperation with an optical imaging sorting machine (not shown), analyzes the first time of travel $t_1$ and all other collected/gathered data related to the individual objects of interest 11 passing through the inspection zone 18 including, but not limited to, the second time of travel $t_2$ and "compiles" the information together. If the controller 60, does not receive information from the imaging and sorting system (not shown) that indicates presence of an object of interest 11 within the inspection zone 18 and yet the controller 60 also determines a second time of travel $t_2$ or the controller 60 determines there is an identified moving location that generates an absence of reflected electromagnetic radiation wave/pulse 31 which is evidence of the presence of an "indistinguishable" or "invisible" object within the inspection zone 18, the controller 60 will generate an ejection signal 61 that is communicated to the ejector 50 to cause the ejector 50 to release a burst of high pressure air 57 through at least one of the air discharge nozzles 52 to strike the "invisible" object of interest 11 and cause the "invisible" object of interest 11 to move into the second path of travel 55 which is different than the first path of travel 15 so that the "invisible" object is directed to a receiver 56 of unacceptable objects 13 and separated from the acceptable objects 12 within the stream of objects of interest 11.

Therefore it will be seen that the present invention provides a convenient method and apparatus whereby otherwise "indistinguishable" or "invisible" or "not machine visually perceptible" products and/or unacceptable objects 13 which are admixed within a product stream of individual objects of interest 11 can be sorted with a high degree of efficiency. The present invention, when rendered operational can use multiple different sources of electromagnetic radiation which can be directed toward the objects of interests 11.

In a first aspect, the present invention relates to a method for detecting objects of interest 11 that includes the steps of releasing a stream of individual objects of interest 11 from a conveying device 14 into an unsupported gravity influenced path of travel 15; providing an inspection zone 18 having opposite first 19 and second sides 20 and opposite first and second edges 20A, 20B respectively, and locating the inspection zone 18 downstream of a position where the stream of individual objects of interest 11 are released for movement along the unsupported path of travel 15, and orienting the path of travel 15 so that the path of travel 15 passes through the inspection zone 18 and between the opposite first 19 and second sides 20 and first and second edges 20A, 20B thereof; positioning an electromagnetic radiation emitter 25 on the first side 19 of the inspection zone 18, and further periodically energizing the electromagnetic radiation emitter 25 to generate a pulsed emission of electromagnetic radiation 26 which traverses the inspection zone 18, and directing the emitted electromagnetic radiation pulse 26 towards the second side 20 of the inspection zone 18, and wherein at least a portion of the emitted electromagnetic radiation pulse 26 strikes at least one of the individual objects of interest 11 traveling along the unsupported path of travel 15, and through the inspection zone 18; positioning a reflective background 40 adjacent to the second side 20 of the inspection zone 18 and at a known distance 27 from the electromagnetic radiation emitter 25, and wherein the reflective background 40 reflects at least a portion of the emitted electromagnetic radiation pulse 26 back in the direction of the first side 19 of the inspection zone 18; providing an electromagnetic radiation detector 30, and positioning the electromagnetic radiation detector 30 on the first side 19 of the inspection zone 18, and at a known distance 32 from the reflective background 40, and wherein the electromagnetic radiation detector 30 receives, and detects, at least a portion of the reflected electromagnetic radiation pulse 31 which is emitted by the periodically energized electromagnetic radiation emitter 25, and which has further been reflected, at least in part, back in the direction of the first side 19 of the inspection zone 18 by either the reflective background 40, or by at least one of the individual objects of interest 11, as the respective objects of interest 11 pass through the inspection zone 18 and along the unsupported path of travel 15; providing a controller 60 and operatively coupling the controller 60 with both the electromagnetic radiation emitter 25 and the electromagnetic radiation detector 30; determining by use of the controller 60, a first time of travel $t_1$ for each of the emitted electromagnetic radiation pulses 26 to travel from the periodically energized electromagnetic radiation emitter 25 the known distance 27 to the reflective background 40 and to travel the known distance 32 from the reflective background 40 to the electromagnetic radiation detector 30 after being at least partially reflected by the reflective background 40; determining by use of the controller 60, a second time of travel $t_2$ for each emitted electromagnetic radiation pulse 26 which is directed towards, and strikes at least one of the respective objects of interest 11 moving through the inspection zone 18 along the unsupported path of travel 15, to travel from the electromagnetic radiation emitter 25 to the at least one object of interest 11 in the inspection zone 18 and to travel from at least one object of interest 11 in the inspection zone 18 back to the electromagnetic radiation detector 30, and which second time of travel $t_2$ varies from the first time of travel $t_1$; and determining, by use of the controller 60, the presence of an object of interest 11 within the inspection zone 18 when any determined time varies from the determined first time of travel $t_1$.

A second aspect of the present invention relates to a method for detecting objects of interest 11 passing through an inspection zone 18 having the steps of; providing a stream of individual objects of interest 11, and wherein each of the individual objects of interest 11 have a multitude of characteristics, and wherein the multitude of characteristics of the individual objects of interest 11 in the stream are selected from the group comprising color, length, width, depth, thickness, shape, light polarization, florescence, surface texture, reflectivity, light absorbance, light translucence, and wherein the characteristics can be formed from electromagnetic radiation which is spectrally reflected, refracted, absorbed or transmitted; moving the stream of individual objects of interest 11 along a first supported path of travel from a first position 14A to a second position 14B, and wherein the step of moving the stream of individual objects of interest 11 to the inspection zone 18 further comprises releasing the stream of individual objects of interest 11 from the second position 14B into an unsupported path of travel 15 through the inspection zone 18 that has spaced apart and opposing first 19 and second sides 20 and spaced apart opposing first 20A and seconds 20B edges; providing an electromagnetic radiation emitter 25 adjacent the first side 19 of the inspection zone 18 that, when actuated, generates pulses of electromagnetic radiation 26 which are directed toward the opposing second side 20 of the inspection zone 18 and toward the unsupported moving stream of individual objects of interest 11 so that the electromagnetic radiation pulses 26 impact one or more of the individual objects of interest 11 passing through the inspection zone 18, or the electromagnetic radiation pulses 26 pass completely through the unsupported stream 15 and strike a reflective background 40 which is positioned adjacent the second side 20 of the inspection zone 18 and at a known distance 27 from the electromagnetic radiation emitter 25, and the electromagnetic radiation pulses 26 striking the reflective background 40 are at least partially reflected back toward the first side 19 of the inspection zone 18; providing an electromagnetic radiation detector 30 positioned adjacent the first side 19 of the inspection zone 18 and oriented to receive reflected electromagnetic radiation pulses 31 reflected by the reflective background 40 and reflected by striking at least one of the individual objects of interest 11 within the inspection zone 18, and the electromagnetic radiation detector 30 is positioned a known distance 32 from the reflective background 40; providing a controller 60 operative communicating with the electromagnetic radiation emitter 25 and operatively communicating with the electromagnetic radiation detector 30 to provide emission sync signals 29 to the electromagnetic radiation emitter 25 and to receive reflection receipt signals 41 from the electromagnetic radiation detector 30 so as to determine a time duration between emission of electromagnetic radiation pulses 26 from the emitter 25, and receipt of reflected electromagnetic radiation pulses 31 by the detector 30, and wherein any determined time duration that varies from a known time duration for the emitted electromagnetic radiation pulses 26 to travel both from the emitter 25 to the reflective background 40 and from the reflective background 40 back to the detector 30 indicates an object of interest 11 is present within the inspection zone 18; forming in real time, a multiple aspect representation of the individual objects of interest 11 moving in the unsupported path of travel 15 within the inspection zone 18 with the controller 60 by using reflection receipt signals 41 generated by the electromagnetic radiation detector 30 and wherein the multiple aspect representation has a plurality of features formed from a multitude of electromagnetic wave lengths detected by the electromagnetic radiation detector 30; comparing, with the controller 60, identified characteristics of each of the individual objects of interest 11 in the unsupported path of travel 15 of objects of interest 11 within the inspection zone 18 to a predetermined list of acceptable and unacceptable characteristics maintained within a database (not shown) accessible by the controller 60 in order to make a sorting decision for sorting the objects of interest 11 within the unsupported path of travel 15; and providing an ejector 50 having a multiplicity of individual high pressure air nozzles 52 coupled with a source of high pressure air and which further is positioned downstream of the inspection zone 18 and wherein the ejector 50 is operatively coupled with the controller 60 which individually activates and deactivates one or more of the individual high pressure air nozzles 52 and wherein the activated individual high pressure air nozzles 52, upon receiving an ejection signal 61 releases a stream of high pressure air 57 which strikes and removes identified individual objects of interest 11 from the unsupported path of travel 15 that have been identified by the controller 60 as having predetermined unacceptable characteristics during the unsupported path of travel 15 based, at least in part upon, the multiple aspect representation formed by the controller 60, in real time, as the individual objects of interest 11 pass through the inspection zone 18.

A third aspect of the present invention relates to a method of detecting objects passing through an inspection zone 18 wherein the controller 60 learns that repetitive infinite measures 75 that repetitively occur at an identified location 76 on the reflective background 40 (FIG. 4) which generate no reflection signal 31 (identified on FIG. 4 as time $t_3$), may represent a defect (such as but not limited to a hole) in the reflective background 40, and therefore that repeated infinite measures 75 that repeatedly occurring at that identified location 76 should be disregarded by the controller 60 when a sorting decision is made.

A fourth aspect of the present invention relates to an apparatus for detecting objects of interest 11 passing through an inspection zone 18 and comprises a device 14 for conveying a stream of individual objects of interest 11 and for releasing the stream of individual objects of interest 11 into a gravity influenced unsupported path of travel 15; an inspection zone 18 having opposite first 19 and second 20 sides and opposite first 20A and seconds 20B edges, and which is located downstream of the device 14 for conveying the stream of individual objects of interest 11, and wherein the path of travel 15 passes through the inspection zone 18 between the opposite first 19 and second sides 20 and opposite first 20A and seconds 20B edges thereof; an emitter of pulsed electromagnetic radiation 25 positioned on the first side 19 of the inspection zone 18, and which further, when periodically energized, emits a pulse of electromagnetic radiation 26 which traverses the inspection zone 18, and is further directed towards the opposite, second side 20 of the inspection zone 18, and wherein at least a portion of the emitted electromagnetic radiation pulse 26 strikes at least one of the individual objects of interest 11 traveling along the unsupported path of travel 15 through the inspection zone 18; a reflective background 40 positioned adjacent to the second side 20 of the inspection zone 18, and wherein the reflective background 40 is located at a known distance 27 from the electromagnetic radiation emitter 25, and further the reflective background 40 reflects at least a portion of the emitted electromagnetic radiation pulses 26 that strike the reflective background 40 back in the direction of the first side 19 of the inspection zone 18; an electromagnetic radiation detector 30 positioned on the first side 19 of the inspection zone 18 which receives, and detects, at least a portion of the electromagnetic radiation pulses 26 which are emitted by the periodically energized electromagnetic radiation emitter 25, and which have further been reflected, at least in part, back in the direction of the first side 19 of the inspection zone 18 by either the reflective background 40, or by at least one of the individual objects of interest 11, as the objects of interest 11 pass through the inspection zone 18, and along the unsupported path of travel 15, and wherein a first time of travel $t_1$ is determined for each emitted electromagnetic radiation pulse 26 to travel from the periodically energized electromagnetic radiation emitter 25 the known distance 27 to the reflective background 40 and to travel the known distance 32 from the reflective background 40 to the electromagnetic radiation detector 30 after being, at least partially, reflected by the reflective background 40, and wherein a second time of travel $t_2$ is determined for each emitted electromagnetic radiation pulse 26 to travel from the periodically energized electromagnetic radiation emitter 25 to an object of interest 11 moving along the unsupported path of travel 15 and to be reflected therefrom, and to travel back to the electromagnetic radiation detector 30 and wherein the second time of travel $t_2$ varies from the first time of travel $t_1$; a controller 60 operatively coupled with both the electromagnetic radiation emitter 25 and the electromagnetic radiation detector 30, and wherein any time of travel which varies from the first time of travel $t_1$ is data provided to the controller 60 that is indicative of machine imperceptible or indistinguishable object of interest 11 within the inspection zone 18; and an ejector 50 having a multiplicity of individual high pressure air nozzles 52, coupled with a source of high pressure air and which further is positioned downstream of the inspection zone 18, and wherein the ejector 50 is operatively coupled with the controller 60 which individually activates and deactivates one or more of the individual high pressure air nozzles 52 of the ejector 50, and wherein the activated individual high pressure air nozzles 52 release a burst of high pressure air 57 which strikes and removes individual objects of interest 11 from the stream of objects of interest that have been identified as having predetermined unacceptable characteristics 13 during the unsupported path of travel 15, and also removes individual objects of interest 11 from the stream that are indistinguishable from the reflective background 40.

We claim:

1. A method for detecting objects passing through an inspection zone comprising:

providing an inspection zone having a first side and an opposing second side, and wherein the opposing second side is spaced apart from the first side by a known and predetermined distance;

providing a reflective background at the opposing second side of the inspection zone;

providing a stream of individual objects of interest and moving the stream of individual objects of interest along a first supported path of travel from a first position to a second position, and releasing the stream of individual objects of interest from the second position into an unsupported path of travel so that the stream of individual objects of interest pass through the inspection zone, between the first side and the opposing second side thereof, generally vertically under the influence of gravity;

providing an emitter of pulsed electromagnetic radiation at the first side of the inspection zone that, when actuated, generates pulses of electromagnetic radiation which are directed across the inspection zone and toward the reflective background at the opposing second side of the inspection zone and toward the stream of individual objects of interest passing through the inspection zone so that at least a portion of the emitted pulses of electromagnetic radiation pass through the stream of individual objects of interest and strike the reflective background, or at least a portion of the emitted pulses of electromagnetic radiation impact one or more of the individual objects of interest within the inspection zone, and the emitted electromagnetic radiation pulses that strike the reflective background are at least partially reflected, and the emitted electromagnetic radiation pulses that impact one or more of the individual objects of interest within the inspection zone are at least partially reflected;

providing a detector of electromagnetic radiation positioned at the first side of the inspection zone and oriented to receive electromagnetic radiation pulses that are reflected by the reflective background and that are reflected by striking individual objects of interest within the inspection zone, and the detector of electromagnetic radiation is positioned a known distance from the reflective background and wherein the detector of electromagnetic radiation generates a reflection receipt signal upon detection of a reflected electromagnetic radiation pulse that has been at least partially reflected from the reflective background, and the detector of electromagnetic radiation generates a reflection receipt signal upon detection of a reflected electromagnetic radiation pulse that has been at least partially reflected from an individual object of interest within the inspection zone;

providing a controller operatively communicating with the detector of electromagnetic radiation to receive reflection receipt signals therefrom, and wherein the controller periodically generates an emission signal which is communicated to the emitter of electromagnetic radiation which responsively causes the emitter of electromagnetic radiation to emit a pulse of electromagnetic radiation directed toward the reflective background at the second side of the inspection zone and wherein the controller determines a time duration between each emission signal communicated to the emitter of electromagnetic radiation and each reflection receipt signal received from the detector of electromagnetic radiation, and wherein any determined time duration that varies from a known time duration for each emitted pulse electromagnetic radiation to travel from the electromagnetic radiation emitter to the reflective background and to travel from the reflective background to the detector of electromagnetic radiation is evidence that an object of interest is present in the inspection zone.

2. The method of claim 1 and further comprising:

determining by use of the controller, a first time of travel for each pulse of emitted electromagnetic radiation to travel from the periodically energized emitter of electromagnetic radiation the known distance to the reflective background and to travel the known distance from the reflective background to the detector of electromagnetic radiation after being at least partially reflected by the reflective background;

determining by use of the controller, a second time of travel for each pulse of emitted electromagnetic radiation which is directed towards, and strikes at least one of the respective objects of interest moving along the path of travel, and within the inspection zone, to travel from the periodically energize emitter of electromagnetic radiation to the at least one object of interest, and to travel from the at least one object of interest to back to the detector of electromagnetic radiation, and which second time of travel varies from the first time of travel; and determining the presence of an object of interest with the inspection zone when the determined second time of travel varies from the determined first time of travel.

3. The method of claim 1 and wherein each of the individual objects of interest in the stream has a multitude of characteristics, and wherein the multitude of characteristics of the individual objects of interest in the stream are selected from the group comprising color; length; width; depth; thickness; shape; light polarization; fluorescence; surface texture; reflectivity; light absorbance; light translucence, and wherein the characteristics can be determined from electromagnetic radiation which is spectrally reflected, refracted, absorbed or transmitted.

4. The method of claim 1 and wherein the controller compares determined identified characteristics of the individual objects of interest in the stream that are identified by detected reflected electromagnetic radiation to a predetermined list of desirable and undesirable characteristics of objects of interest in the stream to provide a basis for sorting of the objects of interest in the stream.

5. The method of claim 4 and further comprising:

providing an ejector having a multiplicity of individual high pressure air nozzles, coupled with a source of high pressure air and which further is positioned downstream of the inspection zone, and wherein the ejector is operatively coupled with the controller which individually activates and deactivates the individual high pressure air nozzles, and wherein the activated individual high pressure air nozzles release a stream of high pressure air which removes identified individual objects of interest from the stream of objects of interest that have been identified as having predetermined undesirable characteristics during the unsupported path of travel.

6. The method of claim 1 and further comprising:
providing plural emitters of electromagnetic radiation, and wherein each of the plural emitters of electromagnetic radiation emit an identified spectrum of wavelengths of electromagnetic radiation.

7. The method of claim 6 and further comprising:
providing plural detectors of electromagnetic radiation, and each of the plural detectors of electromagnetic radiation receives an identified spectrum of reflected wavelengths of electromagnetic radiation.

8. The method of claim 7 and further comprising:
forming a multiple aspect representation of each of the individual objects of interest passing through the inspection zone with the controller by using signals generated by the detector of electromagnetic radiation and wherein each multiple aspect representation has a plurality of features formed from the multitude of characteristics detected by the detector of electromagnetic radiation; and
sorting the individual objects of interest from the stream of individual objects of interest based, at least in part, upon the multiple aspect representation formed by the controller, after the individual objects of interest pass through the inspection zone.

9. The method of claim 3 and wherein the emitted electromagnetic radiation has a multitude of individual wavelengths and various of the wavelengths interact uniquely with various of the individually identifiable characteristics of the individual objects of interest in the product stream so as to uniquely identify various of the individually identifiable characteristics based at least in part upon the interaction of the electromagnetic wavelengths with the individually identifiable characteristics.

10. The method of claim 9 and wherein the reflective background is configured to reflect only select wavelengths of electromagnetic radiation back toward the detector so that other of the various wavelengths of electromagnetic radiation emitted by the emitter are usable to determine and identify characteristics of the individual objects of interest in the stream.

11. The method of claim 1 and wherein the signals communicated by the controller to the emitter of electromagnetic radiation and received from the detector are evaluated by the controller examining an initial leading edge of each signal.

12. The method of claim 3 and further comprising:
comparing, with the controller, identified multitude of characteristics of the individual objects of interest in the stream to a predetermined list of acceptable and unacceptable characteristics of objects in the stream to provide a basis for sorting of the objects of interest in the stream, and forming in real time, a multiple aspect representation of the individual objects of interest in the inspection zone with the controller by using signals generated by the detector and wherein the multiple aspect representation has a plurality of features formed from the multitude of electromagnetic wavelengths detected by the detector; and
providing an ejector having a multiplicity of individual high pressure air nozzles, coupled with a source of high pressure air and which further is positioned downstream of the inspection zone, and wherein the ejector is operatively coupled with the controller which individually activates and deactivates one or more of the individual high pressure air nozzles of the ejector, and wherein the activated individual high pressure air nozzles release a stream of high pressure air which strikes and removes identified individual objects of interest from the stream of objects of interest that have been identified as having predetermined unacceptable characteristics during the unsupported path of travel based, at least in part, upon the multiple aspect representation formed by the controller, in real time, as the individual objects of interest pass through the inspection zone.

13. The method of claim 5 and further comprising:
determining by use of the controller, a path of travel for each pulse of emitted electromagnetic radiation which is directed towards the reflective background which strikes at least one of the individual objects of interest moving along the path of travel within the inspection zone, to travel from the periodically energize emitter of electromagnetic radiation to the at least one object of interest; and to travel from the at least one object of interest to back to the detector of electromagnetic radiation
determining with the controller the present position and predicted future positions of the individual object of interest that was struck by the pulse of emitted electromagnetic radiation; and
communicating the present position and the predicted future positions of the individual object of interest to the ejector so as to allow the ejector to remove the individual object of interest from the stream of individual objects of interest.

* * * * *